United States Patent
Nielson (10) Patent No.: US 6,416,492 B1
(45) Date of Patent: Jul. 9, 2002

(54) RADIATION DELIVERY SYSTEM UTILIZING INTRAVASCULAR ULTRASOUND

(75) Inventor: Eric D. Nielson, Bellevue, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 103 days.

(21) Appl. No.: 09/672,423

(22) Filed: Sep. 28, 2000

(51) Int. Cl.[7] .................... A61B 17/20; A61N 5/00
(52) U.S. Cl. .................... 604/22; 600/3; 600/439; 600/467
(58) Field of Search ................ 600/3, 467, 439; 604/22

(56) References Cited

U.S. PATENT DOCUMENTS

| | | | |
|---|---|---|---|
| 5,010,886 A | 4/1991 | Passafaro et al. | 128/660.03 |
| 5,125,137 A | 6/1992 | Corl et al. | 29/25.35 |
| 5,131,397 A | 7/1992 | Crowley | 128/662.06 |
| 5,199,939 A | 4/1993 | Dake et al. | 600/3 |
| 5,213,561 A | 5/1993 | Weinstein et al. | 600/7 |
| 5,243,988 A | 9/1993 | Sieben et al. | 128/662.06 |
| 5,269,291 A | 12/1993 | Carter | 128/24 |
| 5,302,168 A | 4/1994 | Hess | 600/3 |
| 5,307,816 A | 5/1994 | Hashimoto et al. | 128/660.03 |
| 5,318,014 A | 6/1994 | Carter | 604/2 |
| 5,329,194 A | 7/1994 | Dow et al. | 310/17 |
| 5,353,798 A | 10/1994 | Sieben | 128/662.06 |
| 5,362,309 A | 11/1994 | Carter | 604/22 |
| 5,402,789 A | 4/1995 | Dow et al. | 128/660.1 |
| 5,431,663 A | 7/1995 | Carter | 606/128 |
| 5,445,155 A | 8/1995 | Sieben | 129/660.07 |
| 5,454,373 A | 10/1995 | Koger et al. | 128/662.06 |
| 5,474,531 A | 12/1995 | Carter | 604/22 |
| 5,495,852 A | 3/1996 | Stadler et al. | 128/660.07 |
| 5,546,948 A | 8/1996 | Hamm et al. | 128/622.06 |
| 5,620,479 A | 4/1997 | Diederich | 607/97 |
| 5,725,568 A | 3/1998 | Hastings | 623/1 |
| 5,735,811 A | 4/1998 | Brisken | 604/22 |
| 5,840,031 A | * 11/1998 | Crowley | 600/440 |
| 5,842,994 A | 12/1998 | TenHoff et al. | 600/466 |
| 5,876,343 A | 3/1999 | Teo | 600/443 |
| 5,885,218 A | 3/1999 | Teo et al. | 600/443 |
| 5,921,934 A | 7/1999 | Teo | 600/468 |
| 5,976,107 A | 11/1999 | Mertens et al. | 604/96 |

(List continued on next page.)

FOREIGN PATENT DOCUMENTS

| | | |
|---|---|---|
| DE | 197 24 223 C1 | 12/1998 |
| EP | 0 688 580 A1 | 12/1995 |
| JP | 2000024001 | 1/2000 |

(List continued on next page.)

OTHER PUBLICATIONS

Pat. appln. Ser. No. 09/672,569, entitled Computer Controlled Radiation Delivery System Utilizing IVUS, filed on Sep. 28, 2000, is related to U.S. Pat. appln. No. 09/672,423, entitled Radiation Delivery System.

Primary Examiner—William Wayner
(74) Attorney, Agent, or Firm—Crompton, Seager & Tufte, LLC (57) ABSTRACT

A radiation delivery system including a catheter shaft having a distal head. A fixed or removable radiation source is disposed adjacent the distal head. The distal head includes a radiation shield having a window and an ultrasonic transducer. The ultrasonic transducer provides a signal indicative of relative position, tissue geometry and/or tissue characteristics, which may be utilized to determine the appropriate placement of the radiation shield window such that only selected portions of the treatment site are exposed to radiation. The radiation delivery system may include a drive means coupled to the distal head to facilitate rotation thereof. The rotatable head may be rotated at a constant velocity or at a velocity which varies as a function of the signal (e.g., distance from the vascular wall and/or stenotic thickness).

35 Claims, 4 Drawing Sheets

U.S. PATENT DOCUMENTS

| | | | |
|---|---|---|---|
| 6,033,357 A | 3/2000 | Ciezi et al. | 600/3 |
| 6,050,946 A | 4/2000 | Teo | 600/443 |
| 6,050,949 A | 4/2000 | White et al. | 600/466 |
| 6,083,167 A | 7/2000 | Fox et al. | 600/439 |
| 6,090,035 A | 7/2000 | Campbell et al. | 600/7 |
| 6,099,455 A | 8/2000 | Columbo et al. | 600/3 |
| 6,102,862 A | 8/2000 | Grunwald et al. | 600/447 |
| 6,106,454 A | 8/2000 | Berg et al. | 600/3 |
| 6,110,097 A | 8/2000 | Hastings et al. | 600/3 |
| 6,117,065 A | 9/2000 | Hastings et al. | 600/3 |
| 6,120,455 A | 9/2000 | Teo | 600/468 |
| 6,142,926 A | 11/2000 | Schneiderman | 600/3 |
| 6,146,322 A | 11/2000 | Papirov et al. | 600/3 |
| 6,149,574 A | 11/2000 | Trauthen et al. | 600/3 |
| 6,149,575 A | 11/2000 | Leonhardt | 600/4 |
| 6,152,869 A | 11/2000 | Park et al. | 600/3 |
| 6,152,877 A | 11/2000 | Masters | 600/437 |
| 6,162,165 A | 12/2000 | Apple et al. | 600/3 |
| 6,165,440 A | 12/2000 | Esenaliev | 424/11 |
| 6,179,768 B1 | 1/2001 | Loffler et al. | 600/7 |
| 6,264,595 B1 | 1/2001 | Delfino et al. | 600/1 |
| 6,196,963 B1 * | 3/2001 | Williams | 600/3 |
| 6,200,256 B1 | 3/2001 | Weinberger | 600/3 |
| 6,200,257 B1 | 3/2001 | Winkler | 600/3 |
| 6,200,307 B1 | 3/2001 | Kasinkas et al. | 606/7 |
| 6,203,485 B1 | 3/2001 | Urick | 604/104 |
| 6,213,976 B1 | 4/2001 | Trerotola | 604/104 |
| 6,217,503 B1 | 4/2001 | Weinberger et al. | 600/3 |
| 6,224,535 B1 | 5/2001 | Chiu et al. | 600/3 |
| 6,224,536 B1 | 5/2001 | Pike | 600/3 |
| 6,231,494 B1 | 5/2001 | Verin et al. | 600/1 |
| 6,231,495 B1 | 5/2001 | Denk | 600/1 |
| 6,231,719 B1 | 5/2001 | Garvey et al. | 162/109 |
| 6,234,951 B1 | 5/2001 | Hastings | 600/3 |
| 6,234,952 B1 | 5/2001 | Lipric | 600/3 |
| 6,238,332 B1 | 5/2001 | Kanesaka | 600/3 |
| 6,241,719 B1 | 6/2001 | Wallace et al. | 604/509 |
| 6,248,057 B1 | 6/2001 | Mavity et al. | 600/3 |
| 6,251,059 B1 | 6/2001 | Apple et al. | 600/3 |
| 6,254,552 B1 | 7/2001 | Lewis et al. | 600/603 |
| 6,258,019 B1 | 7/2001 | Verin et al. | 600/1 |
| 6,261,219 B1 | 7/2001 | Meloul et al. | 600/3 |
| 6,264,579 B1 | 7/2001 | Odai et al. | 474/153 |
| 6,264,596 B1 | 7/2001 | Weadock | 600/3 |
| 6,264,598 B1 | 7/2001 | Armini | 600/3 |
| 6,267,717 B1 | 7/2001 | Stoll et al. | 600/4 |
| 6,267,775 B1 | 7/2001 | Clerc et al. | 606/198 |
| 6,283,910 B1 | 9/2001 | Bradshaw et al. | 600/3 |
| 6,283,911 B1 | 9/2001 | Keren | 600/3 |
| 6,287,249 B1 | 9/2001 | Tam et al. | 600/3 |
| 6,296,603 B1 | 10/2001 | Turnlind et al. | 600/3 |
| 6,302,839 B1 | 10/2001 | Chernomorsky et al. | 600/4 |
| 6,306,073 B1 | 10/2001 | Weinberger | 600/3 |
| 6,306,074 B1 | 10/2001 | Waksman et al. | 600/7 |
| 6,309,339 B1 | 10/2001 | Ciezki et al. | 600/3 |
| 6,293,899 B1 | 11/2001 | Sioshansi et al. | 600/3 |
| 6,312,374 B1 | 11/2001 | von Hoffmann | 600/3 |
| 6,319,190 B1 | 11/2001 | Schmidt et al. | 600/3 |
| 6,322,490 B1 | 11/2001 | Stack et al. | 600/3 |

FOREIGN PATENT DOCUMENTS

| | | | |
|---|---|---|---|
| WO | 94/025106 | 11/1994 | |
| WO | WO 00/32271 | 6/2000 | |
| WO | WO 00/45627 | 8/2000 | |
| WO | WO 00/56249 | 9/2000 | |
| WO | WO 00/69503 | 11/2000 | |
| WO | WO 00/74778 | 12/2000 | |
| WO | WO 00/76557 | 12/2000 | |
| WO | WO 01/14011 A1 | 3/2001 | |
| WO | WO 01/14617 A1 | 3/2001 | |
| WO | WO 01/21106 A1 | 3/2001 | |
| WO | WO 01/21245 A1 | 3/2001 | |
| WO | WO 01/21248 A1 | 3/2001 | |
| WO | WO 01/26734 A1 | 4/2001 | |
| WO | WO 01/47602 A1 | 7/2001 | |
| WO | WO 01/54764 A2 | 8/2001 | |
| WO | WO 01/60443 A1 | 8/2001 | |
| WO | WO 01/62331 A1 | 8/2001 | |
| WO | WO 01/64123 A1 | 9/2001 | |
| WO | WO 01/66188 A1 | 9/2001 | |
| WO | WO 01/85255 A1 | 11/2001 | A61N/5/10 |
| WO | WO 01/87400 A1 | 11/2001 | A61M/29/00 |

* cited by examiner

RADIATION DELIVERY SYSTEM UTILIZING INTRAVASCULAR ULTRASOUND

CROSS REFERENCE TO RELATED APPLICATION

The present application is related to U.S. patent application Ser. No. 09/672,569, entitled COMPUTER CONTROLLED RADIATION DELIVERY SYSTEM, filed on even date herewith, which is herein incorporated by reference.

FIELD OF THE INVENTION

The present invention generally relates to intravascular medical devices. More specifically, the present invention relates to medical devices suitable for intravascular ionizing radiation therapy.

BACKGROUND OF THE INVENTION

Intravascular ionizing radiation therapy is being used increasingly to treat vascular disease. For example, the administration of ionizing radiation has been proposed as both a primary and a secondary therapy for treatment of vascular stenosis (a vascular restriction or narrowing). Clinical studies show that ionizing radiation may be used to inhibit or prevent restenosis after angioplasty.

Vascular restrictions often vary in shape and size, depending on the extent and nature of the disease, in addition to the size and type of vessel affected. In cross-section, the stenotic tissues forming the vascular restrictions often vary in thickness. Such vascular restrictions with varying thickness may require different amounts of radiation exposure, depending on the thickness of the stenotic material and the relative position of the radiation source.

To address this issue, U.S. Pat. No. 6,033,357 to Ciezki et al. propose the use of a radiation delivery device having a window defined by an attenuator for directing radiation emitted from a radiation source. The attenuator alters the radiation exposure pattern such that compensation may be made for any irregular shape of the stenosis or eccentric positioning of the radiation source. In use, a first intravascular ultrasound (IVUS) catheter is inserted into the vascular system to determine the configuration of the vessel wall and the shape of the stenosis. Based on this information, the configuration of the attenuator section is selected to deliver the desired radiation dose profile. The first IVUS catheter is then withdrawn and the radiation delivery system is inserted into the vascular system. A second IVUS catheter is inserted into the radiation delivery system to orient the attenuator such that the window is adjacent the area to receive the most amount of radiation. The second IVUS catheter is then removed from the delivery system and a radioactive wire is inserted into the delivery system until the radioactive portion is positioned within the treatment area. After sufficient time is allowed to emit the proposed dosage, the radiation source is removed from the delivery system.

The Ciezki et al. device inherently relies on maintaining the desired position of the delivery system between withdrawal of the second IVUS catheter and insertion of the radioactive wire. Any difference in position between these two steps will inevitably result in certain portions of the treatment area receiving more or less radiation than intended. Furthermore, if it is necessary to treat other areas of the vasculature, the individual imaging and delivery steps must be repeated in sequence for each area of the vasculature to be treated. Such numerous steps (repositioning, inserting, removing, etc.) complicate the procedure and consume significant operating room/lab time. In addition, the Ciezki et al. device requires many different attenuators to be stocked in a variety of different sizes, shapes, densities and configurations to address different clinical circumstances. Accordingly, it is desirable to provide a radiation delivery system utilizing IVUS technology that is not susceptible to procedural complexities as with the Ciezki et al. system.

SUMMARY OF THE INVENTION

The present invention addresses these shortcomings by providing a radiation delivery system that fully integrates intravascular ultrasound (IVUS) technology. The radiation system includes a catheter having a distal head. A fixed or removable radiation source is disposed in or adjacent to the distal head. The distal head includes a radiation shield having a window and an ultrasonic transducer. The ultrasonic transducer facilitates placement of the radiation shield window, such that only a portion of the treatment site is exposed to radiation.

Specifically, the ultrasonic transducer provides a signal indicative of relative position, tissue geometry and/or tissue characteristics which may be utilized to determine the appropriate placement of the radiation shield window. Placement of the radiation shield window affects the dose administered to different portions of the treatment site. Thus, the dose may be varied to target different areas of the treatment site with the desired radiation dose.

The radiation delivery system may include a drive means coupled to the distal head to facilitate rotation thereof. The distal head may rotate at a constant velocity or at a variable velocity. For example, the distal head may rotate at a velocity which varies as a function of distance from the vascular wall and/or as a function of stenotic thickness.

The radiation delivery system may include a retractable sheath having a distally disposed radiation shield positioned over the radiation source. The retractable sheath may be used to shield radiation during intravascular navigating and positioning of the delivery system to avoid undesired radiation exposure.

The present invention also provides a method of treating a vascular site with ionizing radiation utilizing a radiation system substantially as described above. The catheter is first introduced into the vascular system of the patient and advanced until the distal head is disposed adjacent the treatment site. The ultrasonic transducer is then activated to generate data indicative of relative position, tissue geometry and/or tissue characteristics at the treatment site. The radiation shield window is then moved as a function of the data to selectively expose the treatment site to ionizing radiation. If a rotating shield is used, the velocity of rotation may be varied as a function of the data, (e.g., distance from the vascular wall and/or stenotic thickness).

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
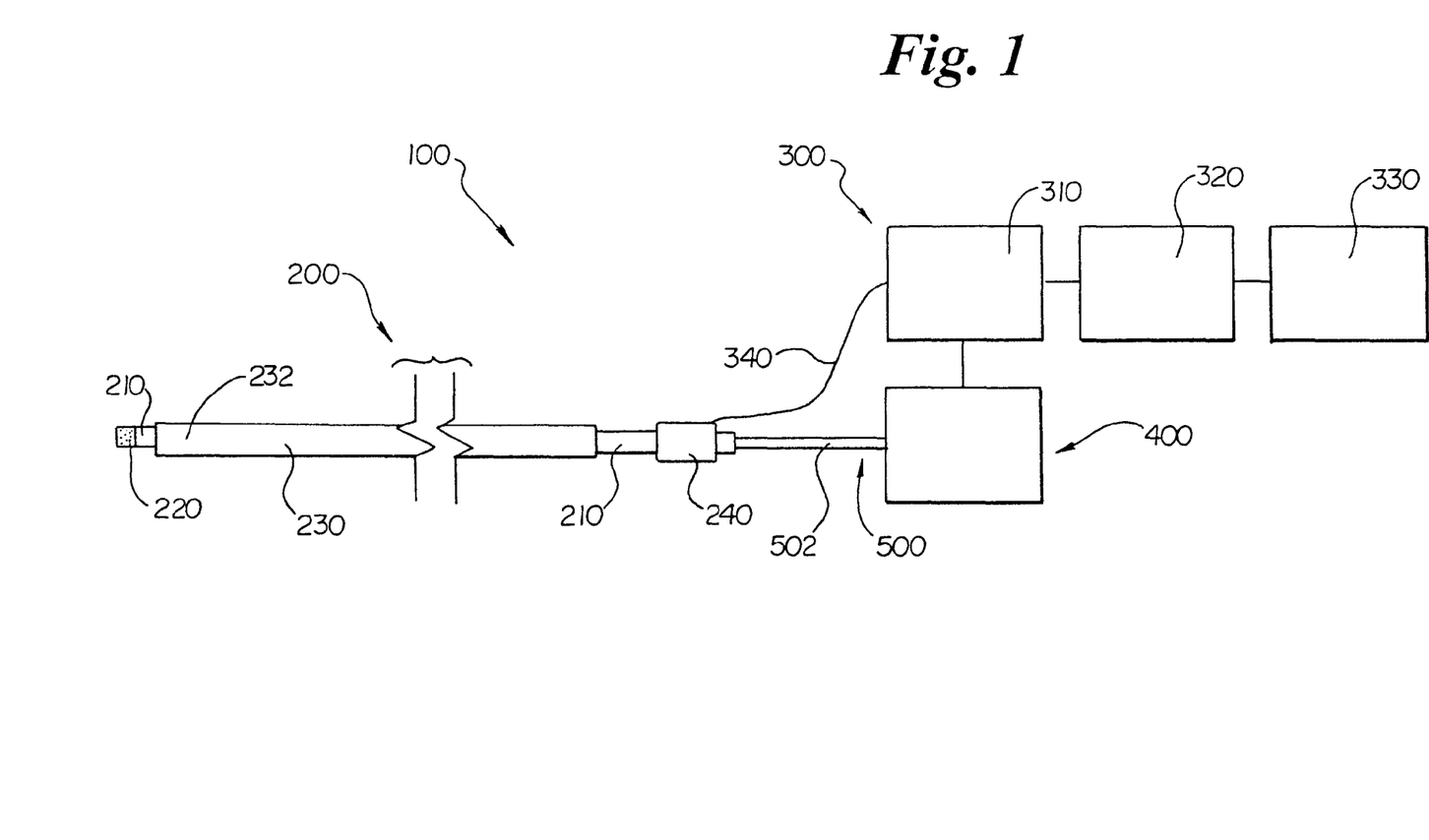
FIG. 1 is a schematic plan view of the intravascular radiation delivery system of the present invention.

Refer now to FIG. 1 which schematically illustrates radiation delivery system 100 of the present invention. Radiation delivery system 100 includes a catheter system 200, an intravascular ultrasound (IVUS) imaging system 300, an afterloader system 400, and a radiation source 500.

Catheter system 200 includes an elongate shaft 210 having a distal head 220. Distal head 220 includes a radiation shield 226 defining a window 224 and an ultrasonic transducer 222, none of which are visible in FIG. 1, but will be described in greater detail with reference to FIGS. 2–6. A retractable sheath 230 having a distally disposed radiation shield 232 may be slidably disposed about the elongate shaft 210. A rotary drive 240 may be connected to the proximal end of the elongate shaft 210. The rotary drive 240 rotates the distal head 220 relative to the elongate shaft 210 by means of a drive cable 242 extending through the shaft 210, which is not visible in FIG. 1, but will be discussed in greater detail with reference to FIG. 2.

IVUS imaging system 300 includes a signal generator/drive control 310, a signal processor 320, and a display/monitor 330. The signal generator/drive control 310 is operatively connected to the rotary drive 240 and the ultrasonic transducer in the distal head 220 by electrical connector/cable 340. Electrical conductors 223, not visible in FIG. 1, extend through the catheter shaft 210 to connect the ultrasonic transducer 222 in the distal head 220 to the cable 340. Except as described herein, IVUS imaging system 300 is generally conventional in design and use. An example of a suitable IVUS imaging system 300 is commercially available from Boston Scientific Corporation. An optical coherence reflectometry (OCR) imaging system may be used in place of IVUS system 300.

Afterloader 400 is also generally conventional except as described herein. Afterloader 400 is used to advance and retract the radiation source wire 500 into and out from the catheter system 200. The radiation source 500 may be fixed or removable. If a removable radiation source 500 is used, as in FIGS. 1, 4, 5 and 6, the radiation source 500 may comprise a conventional elongate wire 502 having a distally disposed ionizing radiation emitter 504. If a fixed radiation source 500 is used, as in FIGS. 2 and 3, the wire 502 is not necessary and the radiation source 500 may simply comprise a conventional ionizing radiation emitter 504 disposed in the distal head 220, with the afterloader 400 directly connected to the catheter 200.

Afterloader 400 may be equipped with a means for measuring the radiation output of the radiation source 500. For example, the radiation output of the radiation emitter 504 may be measured by running the radiation emitter 504 through a ring-shaped Geiger counter. This would allow for greater control of the radiation dose and permit automatic adjustment of the exposure time to compensate for any decay in the radiation emitter 504. This feature would be particularly beneficial if the radiation emitter 504 utilized an isotope with a relatively short half life (e.g., Y90).

Figure 2:
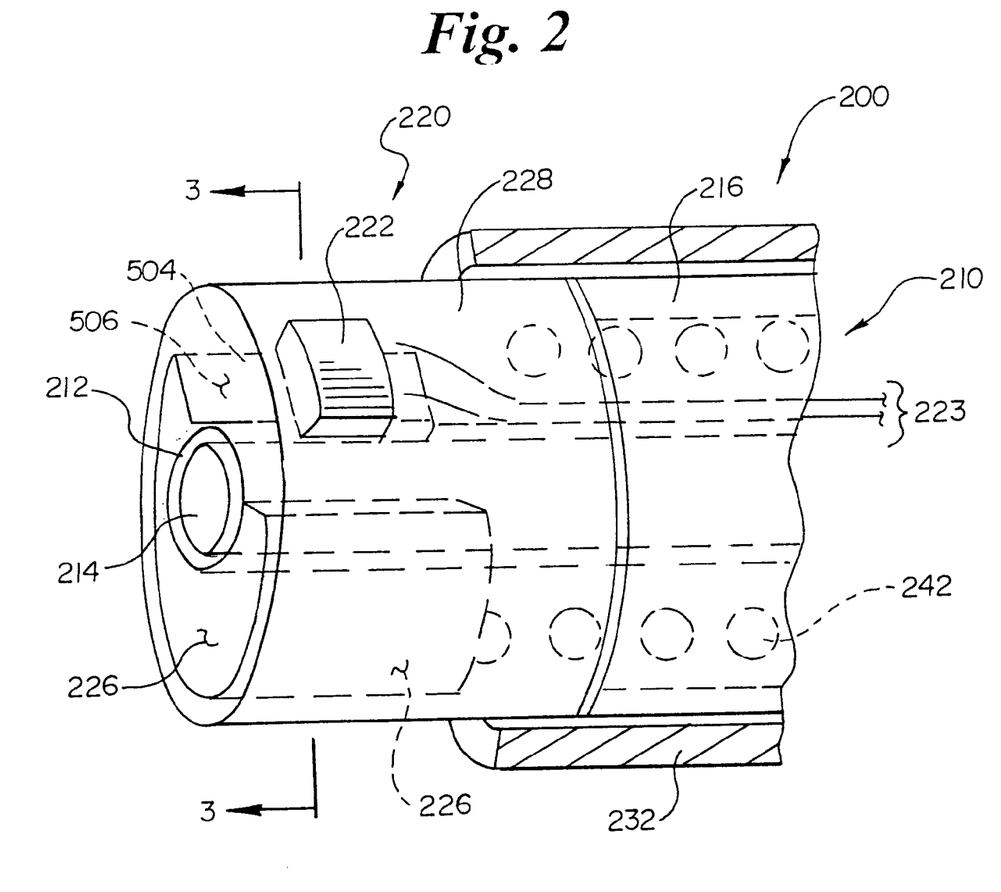
FIG. 2 is a partially sectioned detailed side view of the distal end of the catheter of the system illustrated in FIG. 1.
Figures 3, 5, 6:
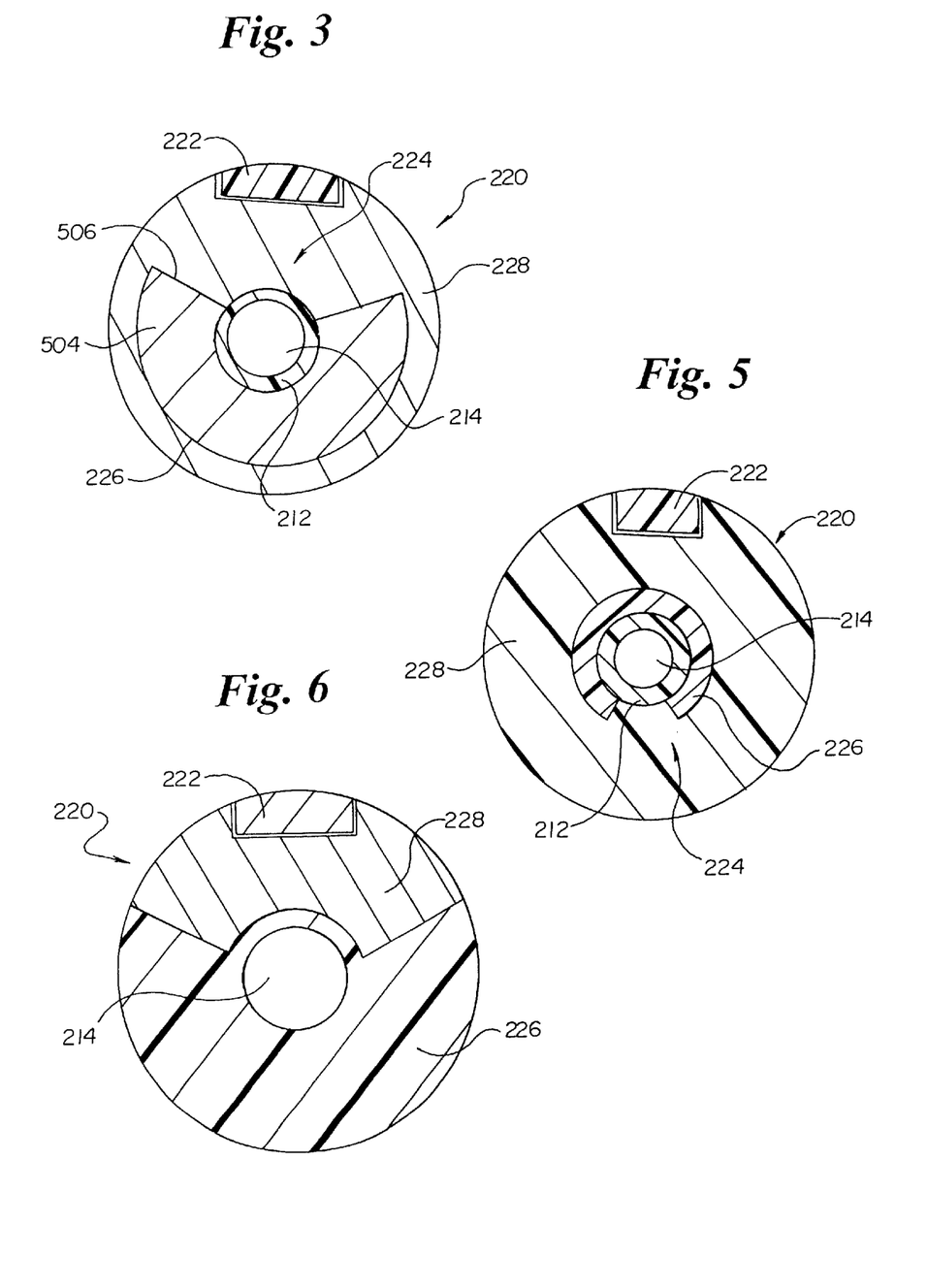
FIG. 3 is a cross-sectional view taken along line 3—3 in FIG. 2.
FIG. 5 is a cross-sectional view taken along line 5—5 in FIG. 4.
FIG. 6 is a cross-sectional view of an alternative embodiment of the distal end illustrated in FIG. 5.

Refer now to FIG. 2 which illustrates a partially sectioned detailed side view of the distal end of the catheter 200, and FIG. 3 which illustrate a cross-sectional view taken along line 3—3 in FIG. 2. The elongate shaft 210 of the catheter 200 includes an inner tube 212 coaxially disposed in an outer tube 216. The inner tube 212 defines a guidewire/radiation source lumen 214. An annular lumen is defined between the inner tube 212 and the outer tube 216 to accommodate the drive shaft 242. The inner tube 212 extends distally beyond the distal end of the outer tube 216 to serve as an axle for the rotatable distal head 220.

The inner tube 212 and the outer tube 216 of the elongate shaft 210 may comprise any conventional shaft material such as a polymer or a reinforced polymer composite. The drive cable 242 may comprise a multi-fillar metal cable or other conventional structure known to those skilled in the art of drive cables utilized in intravascular catheters.

Optionally, the distal end of the inner tube 212 may extend beyond the distal end of the distal head 220 a sufficient distance to define a rapid exchange guidewire lumen (not shown). The inner tube 212 may extend approximately 5 cm beyond the distal end of the head 220 with a guidewire access port defined through the wall of the inner tube 212 approximately 1 cm proximal of the distal end of the inner tube 212. A removable stiffening mandrel may be disposed in the lumen 214 of the inner tube 212 extending from the proximal end of the catheter shaft 210 to a point immediately proximal of the guidewire side port. With this arrangement, the catheter 200 may be operated in the rapid exchange mode or the over the wire mode.

The distal head 220 is rotatably mounted about the inner tube 212 and directly connected to the distal end of the drive shaft 242. The proximal end of the drive shaft 242 is operably connected to the rotary drive 240 which is controlled by the signal generator/drive control unit 310. The drive shaft 242 is freely disposed in the annular lumen defined between the inner tube 212 and the outer tube 216 such that rotation of the drive shaft 242 by rotary drive 240 causes the distal head 220 to rotate about the inner tube 212 relative to the shaft 210.

The distal head 220 includes a transmitting/receiving ultrasonic transducer 222 which is operably connected to the imaging system 300 by way of electrical conductors 223 and cable 340. The electrical conductors 223 may either rotate with the drive cable 242 or remain stationary relative to the elongate shaft 210. In either situation, rotary contacts (not shown) are necessary since the transducer 222 rotates relative to the electrical cable 340. If the electrical conductors 223 rotate with the drive cable 242, rotary contacts may be provided in the rotary drive unit 240. If the electrical conductors 223 remain stationary relative to the drive cable 242, rotary contacts may be provided at the interface between the proximal end of the distal head 220 and the distal end of the elongate shaft 210.

Distal head 220 also includes a fixed radiation emitter 504 and a radiation shield 226. Radiation emitter 504 may comprise any suitable ionizing radiation material including beta and gamma radiation emitting isotopes. Radiation shield 226 may similarly comprise any conventional shielding material that has sufficient density to attenuate radiation emitted from the radiation emitter 504. Those skilled in the art will recognize that many suitable isotopes may be used for radiation emitter 504 and many suitable attenuating materials may be used for radiation shield 226.

In this particular embodiment, the radiation emitter 504 comprises a C-shaped tubular solid element having a semicircular cross-section. The exterior surface of the radiation emitter 504 is coated with a suitable radiation attenuating material to form the radiation shield 226. Preferably, the proximal face, the distal face and the circumferential surface are coated with a radiation attenuating material. Thus, the radiation emitter 504 has an uncoated surface 506 along the edge surfaces and the inside circumferential surface. By providing a radiation shield 226 and radiation emitter 504 in this configuration, a window 224 is defined as best seen in FIG. 3. Window 224 defines the size and geometry of the lateral radiation exposure. The size of the window may be varied by altering the arc angle of the radiation emitter 504 and radiation shield 226. Generally, the smaller the window 224, the greater exposure time necessary to deliver a given dose. Similarly, the larger the window 224 the less exposure time required to deliver a given dose. In addition, the smaller the window 224, the greater the accuracy of delivering the desired dose to a given target site. Thus, the size of the window 224 may be varied depending on the desired level of accuracy balanced with the desired exposure time for a given dose.

The ultrasonic transducer 222 is located at a known position relative to the window 224. Preferably, the ultrasonic transducer 222 is aligned with the window 224. Alternatively, to avoid potential adverse effects of radiation exposure, the transducer 222 may be located 90° or 180° from the window 224. To the extent that transducer 222 comprises a material that attenuates radiation, it may be desirable to locate the transducer 222 outside the exposure range of the window 224. However, the ultrasonic transducer 222 may be located at any position relative to the window 224 as long as the relative position is known.

The components of the distal head 220 are held in place by a housing 228 which comprises a molded polymer or resin. The housing 228 serves to maintain relative alignment of the components, namely the ultrasonic transducer 222, the radiation shield 226 and the radiation emitter 504. Preferably, the housing 228 comprises a material which does not attenuate radiation. Suitable low attenuation materials include polymers, low density metals and alloys, glass, and composites thereof. The entire housing 228 may comprise a low attenuating material, or only the portions within the exposure range of the window 224 may comprise low attenuating material, while the remainder of the housing 228 comprises any suitable material that may attenuate radiation.

The length of the radiation emitter 504 and the corresponding length of the radiation shield 226 may be varied depending on the desired treatment length. For example, if relatively long segments of vasculature are to be treated, the radiation emitter 504 and radiation shield 226 may have a relatively long length on the order of 2 cm to 10 cm. Alternatively, a relatively short radiation emitter 504 and radiation shield 226 may be utilized to treat relatively short vascular segment. Also, a short radiation emitter 504 may be used to sequentially or continuously treat relatively long vascular segments. For example, a short radiation emitter 504 may be rotated and pulled back continuously, thereby tracing a spiral pattern on the inside surface of the artery to treat a long vascular segment in a single pass. A relatively short radiation emitter 504 and radiation shield 226 may, for example, have a length on the order of 0.1 cm to 2 cm.

The catheter 200 may optionally include a retractable sheath 230 coaxially and slidably disposed about the elongate shaft 210. The retractable sheath 230 includes a distal portion 232 which incorporates a radiation shielding material. Preferably, the retractable sheath 230, including the distal radiation shielding portion 232, comprises a relatively flexible polymeric tube. The radiation shielding material on the distal end 232 of the retractable sheath 230 may comprise any suitable material which attenuates radiation, such as a metallic coating on the polymer tube or a heavy metal powder loaded in the polymer tube wall.

In use, the catheter 200 is inserted into the vascular system of the patient and navigated until the distal head 220 is disposed adjacent the treatment site. If a fixed radiation emitter 504 is utilized as in this particular embodiment, the retractable sheath 230 is positioned about the elongate shaft 210 such that the distal shielding portion 232 is disposed about the radiation emitter 504 in order to avoid unnecessary radiation exposure during navigation. The catheter 200 is navigated through the vascular system over a guidewire extending through the lumen 214 of the inner tube 212. As mentioned previously, the catheter 200 may be operated in the over the wire mode or in the rapid exchange mode. Navigation of the catheter 200 may be assisted by conventional radiographic techniques and/or by utilizing the IVUS imaging system 300.

Once in the desired position, the IVUS imaging system 300 may be activated to collect data indicative of the position of the distal head 220 relative to the surrounding tissue, the geometry of the surrounding tissue, and/or the characteristics of the surrounding tissue. This data may be used to determine the thickness of the stenotic material about the circumference of the treatment site and further to determine the relative position of the window 224 relative to the surrounding tissue. This data collection may be conducted with the distal head 220 in the static mode or in the dynamic mode. In the dynamic mode, the distal head 220 rotates at a velocity as dictated by the rotary drive 240 and controlled by the signal generator/drive control unit 310.

For imaging purposes, the distal head 220 may be rotated at a relatively constant velocity to collect data correlating angular position of the transducer 222 and window 224 to the thickness of the stenotic material and the distance to the vascular wall. Utilizing this data, the desired treatment parameters may be selected by the physician. Generally speaking, in the areas having thicker stenotic material, radiation exposure time is relatively longer than the exposure time for thinner stenotic material. In addition, the greater the distance the target treatment site from the radiation emitter 504 and window 224, the greater the exposure time. These variables (stenotic thickness and distance to vascular wall) may be utilized to determine the desired rotational velocity function. The velocity function may be preprogrammed into the signal generator/drive control unit 310 or manually programmed by the treating physician during the procedure.

Once the desired rotational velocity function is determined, the retractable sheath 230 may be retracted in the proximal direction until the distal end of the distal radiation shield 232 is located proximal of the radiation emitter 504. After retracting the sheath 230 to expose the radiation emitter 504, the distal head 220 may be rotated according to the predetermined velocity function for the desired treatment time. After the desired treatment time has expired, (although not necessary, the retractable sheath 230 may be advanced until the radiation shielding portion 232 covers the distal head 220) the entire catheter system 200 may be removed from the patient.

The velocity function for the distal rotating head 220 may be constant or variable. For example, the velocity function may vary as a function of distance from the vascular wall and/or as a function of stenotic thickness. The velocity function may dictate that the rotatable head have a constant velocity within a single revolution but vary over a period of revolutions. Alternatively, the velocity function may dictate that the rotatable head 220 rotate at a velocity that varies within each revolution over a period of revolutions. For example, the distal head 220 may rotate at a relatively slow rate when the window 224 is aligned with relatively thick stenotic material or when the window 224 is relatively far from the vascular wall. In addition, the rotatable head 220 may rotate at a relatively fast rate when the window 224 is aligned with relatively thin stenotic material or when the window 224 is relatively is close to the vascular wall.

Figure 4:
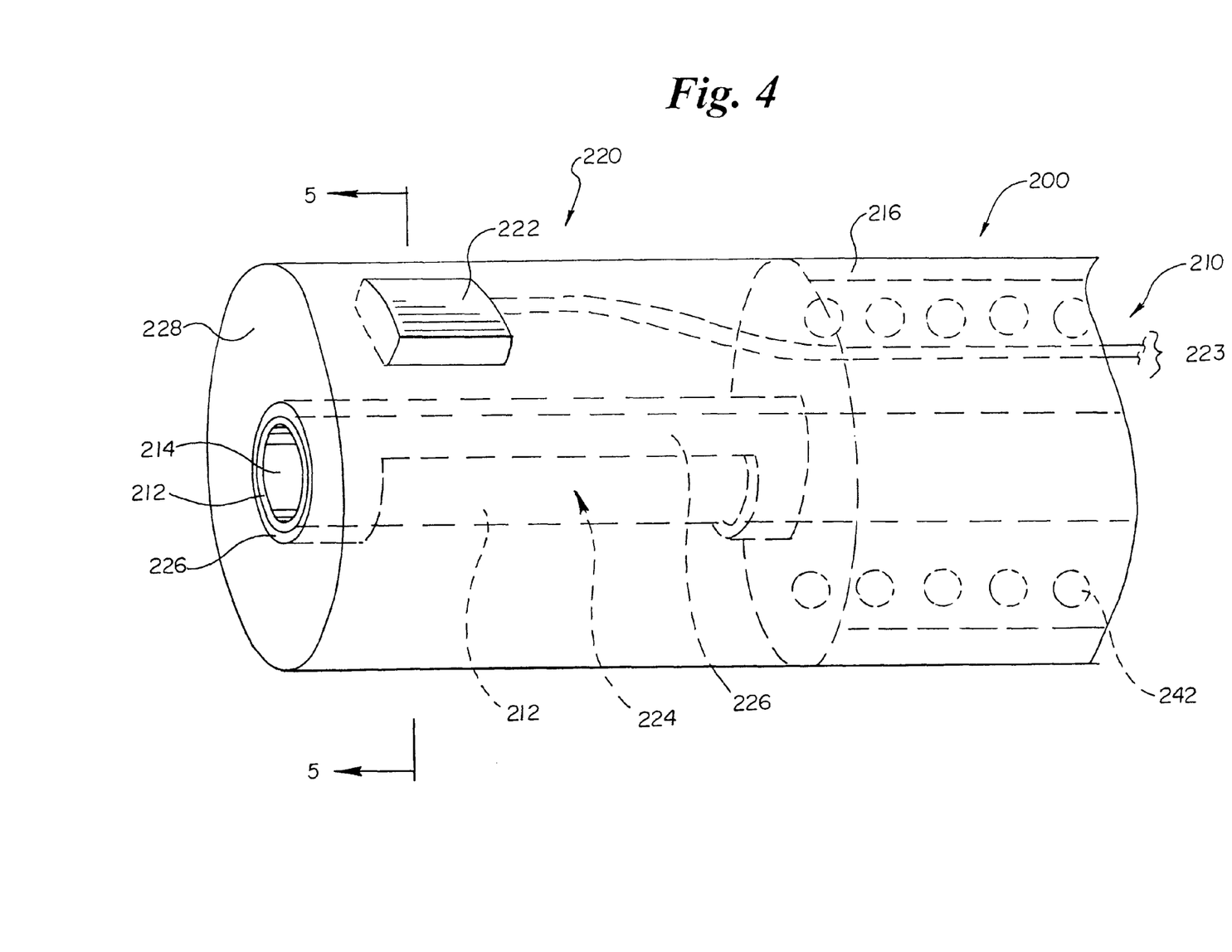
FIG. 4 is a detailed side view of an alternative embodiment of the distal end of the catheter of the system illustrated in FIG. 1.

Refer down to FIG. 4, which illustrates a detailed side view of an alternative embodiment of the distal end of the catheter 200, and FIG. 5 which illustrates a cross-sectional view taken along 5—5 in FIG. 4. Except as described herein, the embodiment of FIGS. 4 and 5 is the same in design and use as the embodiment of FIGS. 2 and 3. The primary difference between the embodiment of FIGS. 2 and 3 and the embodiment of FIGS. 4 and 5 is that the radiation source 500 is removable. Specifically, the embodiment of FIGS. 2 and 3 provided a fixed radiation source 500 comprising a radiation emitter 504 disposed in the distal head 220. By contrast, the radiation source 500 of the embodiment illustrated in FIGS. 4 and 5 is a removable source requiring an elongate delivery wire 502 and an afterloader 400 as discussed previously. One advantage of this embodiment relative to the embodiment, discussed with reference to FIGS. 2 and 3 is that the catheter 200 may be utilized for imaging purposes independent of whether radiation treatment is to be administered.

As seen in FIGS. 4 and 5, the elongate shaft 210 includes an outer tube 216 and an inner tube 212. As in the previously discussed embodiment, the inner tube 212 extends beyond the distal end of the outer tube 216 to the distal end of the distal head 220. However, in this particular embodiment, the radiation shield 226 is disposed about the portion of the inner tube 212 extending through the distal head 220. The radiation shield 226 comprises a tubular structure made of radiation attenuating material having a cut out portion defining a window 224. The radiation shield 226 rotates with the distal head 220 about the inner tube 212. With this arrangement, when the radiation emitter 504 is disposed within the lumen 214 adjacent to the window 224, radiation is shielded around the periphery of the radiation emitter 504 by the shield 226, except in the window portion 224.

This embodiment does not require the use of a retractable shield 230 as discussed with reference to FIGS. 2 and 3. Rather, the catheter 200 of this embodiment may be intravascularly navigated with the radiation source 500 contained within the afterloader 400. After the catheter 200 is navigated to the desired treatment site, the guide wire is withdrawn from the lumen 214 to permit insertion of the radiation source 500. With the distal head 220 is in the desired position and the velocity function and other treatment parameters programmed, the afterloader 400 may be used to advance the radiation source 500 until the radiation emitter 504 is disposed within the distal head 220. The distal head 220 may then be rotated as discussed previously to selectively expose portions of the treatment site to radiation through window 224. After the desired treatment time, the afterloader 400 may be activated to retract the radiation source therein, and the catheter system 200 may be withdrawn.

Refer now to FIG. 6 which illustrates a cross-sectional view of an alternative embodiment of the distal end of the catheter 200 illustrated in FIG. 5. Specifically, FIG. 6 illustrates an alternative arrangement of the components of the distal head 220 used in the embodiment illustrated in FIGS. 4 and 5. Except as described herein, the embodiment of FIG. 6 is the same in design and use as the embodiment of FIGS. 4 and 5.

In the embodiment illustrated in FIG. 6 the inner tube 212 terminates adjacent the distal end of the outer tube 216. The distal head 220 includes a radiation shield 226 which functions as described previously, but also serves to define the lumen 214 within the distal head 220. With this arrangement, the distal head 220 does not rely on the inner tube 212 to serve as an axle for rotation. Rather, the distal head 220 is supported by the drive cable 242 and the radiation source 500 inserted therein.

From the foregoing, it should be apparent that the present invention provides a radiation delivery system 100 that fully integrates an IVUS system 300. Radiation delivery system 100 includes a catheter system 200 including a rotatable distal head 220. A fixed or removable radiation source 500 is disposed in or adjacent to the distal head 220. The distal head 220 includes a radiation shield 226 having a window 224 and an ultrasonic transducer 222 at a known position relative to the window 224. The ultrasonic transducer 222 provides data indictitive of the relative position of the distal head 220 and the geometry and characteristics of the surrounding tissue, which may be utilized to determine the appropriate treatment parameters, including a velocity function for the rotatable distal head 220. Rotatable head 220 may be rotated according to the velocity function which varies according to the distance of the window 224 and radiation emitter 504 from the vascular wall and/or the relative thickness of the stenotic material.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular radiation system for the treatment of a vascular site by ionizing radiation, the radiation system comprising:
   an elongate catheter having a proximal end and a distal end;
   a head disposed on the distal end of the catheter, the head including a radiation shield having a window and an ultrasonic transducer; and
   a radiation source disposed adjacent the radiation shield.

2. An intravascular radiation catheter as in claim 1, wherein the radiation source is fixed relative to the catheter.

3. An intravascular radiation catheter as in claim 1, wherein the radiation source is movable relative to the catheter.

4. An intravascular radiation catheter as in claim 1, wherein the radiation shield is fixed relative to the transducer.

5. An intravascular radiation catheter as in claim 4, wherein the head is rotatable relative to the shaft.

6. An intravascular radiation catheter as in claim 5, further comprising a drive means coupled to the head.

7. An intravascular radiation catheter as in claim 5, wherein the head rotates at a constant velocity.

8. An intravascular radiation catheter as in claim 5, wherein the head rotates at a variable velocity.

9. An intravascular radiation catheter as in claim 8, wherein the vascular site defines a vascular wall and wherein the head rotates at a velocity which varies as a function of distance from the vascular wall.

10. An intravascular radiation catheter as in claim 8, wherein the vascular site defines a stenotic thickness and wherein the head rotates at a velocity which varies as a function of stenotic thickness.

11. An intravascular radiation catheter as in claim 8, wherein the head rotates at a velocity which is constant within a revolution, but varies over a period of revolutions.

12. An intravascular radiation catheter as in claim 8, wherein the head rotates at a velocity which varies within a revolution over a period of revolutions.

13. An intravascular radiation catheter as in claim 4, wherein the ultrasonic transducer is aligned with the window of the radiation shield.

14. An intravascular radiation catheter as in claim 4, wherein the ultrasonic transducer is disposed at an angular position relative to the window of the radiation shield.

15. An intravascular radiation catheter as in claim 14, wherein the angular position is 90 degrees.

16. An intravascular radiation catheter as in claim 14, wherein the angular position is 180 degrees.

17. An intravascular radiation catheter as in claim 4, further comprising a retractable sheath having a distally disposed radiation shield positioned over the radiation source.

18. An intravascular radiation catheter as in claim 4, wherein the catheter shaft includes a guidewire lumen.

19. An intravascular radiation catheter as in claim 18, wherein the guidewire lumen has a proximal end disposed distally of the head.

20. An intravascular radiation catheter as in claim 4, wherein the radiation shield is semi-circular in cross-section.

21. An intravascular radiation catheter as in claim 20, wherein the open portion of the semi-circle is the window.

22. An intravascular radiation catheter as in claim 21, wherein the radiation shield is tubular.

23. An intravascular radiation catheter as in claim 22, wherein the radiation source is disposed in the radiation shield.

24. An intravascular radiation catheter as in claim 4, wherein the radiation source is semi-circular in cross-section.

25. An intravascular radiation catheter as in claim 24, wherein the radiation source is tubular.

26. An intravascular radiation catheter as in claim 25, wherein the radiation shield covers the outer surface of the radiation source.

27. An intravascular radiation catheter as in claim 4, wherein the radiation source comprises an elongate shaft having a distally disposed radiation emitter.

28. An intravascular radiation catheter as in claim 27, wherein the catheter shaft includes a source lumen and wherein the radiation source is disposed therein.

29. A method of treating a vascular site in the vascular system of a patient by ionizing radiation, the method comprising the steps of:

providing an intravascular radiation system comprising an elongate catheter shaft having a proximal end and a distal end, a distal head disposed on the distal end of the shaft, the head including a radiation shield having a window and an ultrasonic transducer, and a radiation source disposed adjacent the radiation shield;

inserting the catheter shaft into the vascular system of the patient;

advancing the catheter shaft until the head is disposed adjacent the treatment site;

activating the ultrasonic transducer to generate data indicative of the nature of the vascular site and/or the position of the head relative to the vascular site; and moving the shield as a function of the data to selectively expose the treatment site to ionizing radiation emitted from the radiation source.

30. A method of treating a vascular site as in claim 29, wherein the head is rotatable and wherein the step of moving the shield comprises rotating the shield.

31. A method of treating a vascular site as in claim 30, wherein the head is rotated at a constant velocity.

32. A method of treating a vascular site as in claim 30, wherein the head is rotated at a variable velocity.

33. An intravascular radiation catheter as in claim 32, wherein the velocity varies as a function of distance from the vascular wall.

34. An intravascular radiation catheter as in claim 32, wherein the velocity varies as a function of stenotic thickness.

35. A method of treating a vascular site as in claim 29, wherein the radiation system includes a retractable sheath having a distally disposed radiation shield initially positioned over the radiation source, the method further comprising the step of moving the sheath to expose the radiation source.

* * * * *